United States Patent [19]

Matsuhashi et al.

[11] Patent Number: 5,073,628

[45] Date of Patent: Dec. 17, 1991

[54] HYPOSENSITIZATION AGENT

[75] Inventors: Tyoku Matsuhashi, Saitama; Mitsuko Usui, Okayama; Masakazu Mitsuhashi, Okayama; Shunsaku Ando, Okayama, all of Japan

[73] Assignee: Kabushiki Kaisha Hayashibara Seibutsu Kagaku Kenkyujo, Okayama, Japan

[21] Appl. No.: 574,713

[22] Filed: Aug. 29, 1990

[30] Foreign Application Priority Data

Sep. 2, 1989 [JP] Japan ................................. 1-228085

[51] Int. Cl.$^5$ ............................................. A61K 39/36
[52] U.S. Cl. ................................... 530/379; 530/370; 530/406; 530/410; 530/411; 530/359; 424/91
[58] Field of Search ............... 530/370, 379, 406, 410, 530/411, 359; 424/91

[56] References Cited

U.S. PATENT DOCUMENTS 4,939,239 7/1990 Matsuhashi et al. ............. 424/91 X

OTHER PUBLICATIONS

Chem. Abstracts, vol. 112, 1990, 62606s, effective date Mar. 22, 1989, Hayashibara.

*Primary Examiner*—Howard E. Schain
*Attorney, Agent, or Firm*—Browdy and Neimark

[57] ABSTRACT

A novel hyposensitization agent was prepared by covalently attaching a saccharide to a cedar pollen allergen having a partial amino acid sequence of Ala-Ile-Asn-Ile-Phe-Asn- beginning at its N-terminal. The hyposensitization agent, when compared with an intact cedar pollen allergen, extremely accelerates the production of immunoglobulin G and M antibodies which are specific to intact cedar pollen allergen, but extremely reduces the production of immunoglobulin E antibody which is specific to the allergen. Thus, the hyposensitization agent is administrable to cedar pollinosis patients with no anaphylaxis and allergy, and cuts hyposensitization period to about 1/3 to 1/200.

27 Claims, No Drawings

HYPOSENSITIZATION AGENT

BACKGROUND OF THE INVENTION

1. Field of the invention

The present invention relates to a hyposensitization agent. More particularly, the present invention relates to a hyposensitization agent comprising a saccharide covalently attached to a cedar pollen allergen having a partial amino acid sequence of Ala-Ile-Asn-Ile-Phe-Asn- beginning at its N-terminal.

2. Abbreviations

Ala: alanine residue
Arg: arginine residue
Asn: asparagine residue
Asp: aspartic acid residue
Gln: glutamine residue
Glu: glutamic acid residue
Gly: glycine residue
Ile: isoleucine residue
Lys: lysine residue
Met: methionine residue
Phe: phenylalanine residue
Pro: proline residue
Ser: serine residue
Trp: tryptophane residue
Tyr: tyrosine residue
Val: valine residue
Each amino acid residue is L-configuration.

3. Description of the prior art

Cedar pollinosis is an allergic disease caused by a cedar pollen scattered from blooming cedars.

Recently, the number of cedar pollinosis patients is gradually increasing in Japan with the increment of areas under cedar afforestation. Although cedar pollinosis seasonally occurs, it is not disregardable in view of the public health.

In conventional therapy, for example, steroid hormone or disodium cromoglycate is administered. Such therapy is a symptomatic treatment which temporally relieves a symptom of a patient.

While administration of intact cedar pollen allergen responsible for cedar pollinosis has been attempted to effect hyposensitization in order to completely cure cedar pollinosis.

Such hyposensitization, however, has the drawbacks that it has a fear of eliciting anaphylaxis from the cedar pollen allergen used, and that treatment using the cedar pollen allergen should be continued for a long time, i.e. about 3 years, because a small amount of the cedar pollen allergen is repeatedly administered to a cedar pollinosis patient in order to avoid such anaphylaxis.

Furthermore, cedar pollen allergen should be carefully handled because it is readily adsorbed on vessels such as glassware and metalware, and, in hyposensitization, this renders the administration of a prescribed amount of cedar pollen allergen very difficult.

SUMMARY OF THE INVENTION

The present inventors studied a modification of cedar pollen allergen in order to obtain a novel hyposensitization agent which can be used in the prevention and treatment of cedar pollinosis, and applied an application of a hyposensitization agent comprising a saccharide covalently attached to a cedar pollen allergen to the Japanese Patent Office. The application has been laid-open under the Japanese Patent Laid-Open No. 156,926/89.

It was revealed that, however, the hyposensitization agent disclosed in the Japanese Patent Laid-Open No. 156,926/89 could relieve the symptom of most pollinosis patients, but could not hyposensitize some pollinosis patients.

As a result, the present inventors studied a cedar pollen allergen per se which was present in a cedar pollen and screened a novel cedar pollen allergen in order to establish a hyposensitization agent comprising a cedar pollen allergen covalently attached to a saccharide.

DETAILED DESCRIPTION OF THE INVENTION

The present invention was made to attain the above object. The present inventors found a novel cedar pollen allergen, more particularly, we found the following findings (i) to (iii), and accomplished the present invention:

(i) A small amount of novel cedar pollen allergen comprising a partial amino acid sequence of Ala-Ile-Asn-Ile-Phe-Asn- beginning at its N-terminal is present in a cedar pollen;

(ii) The novel allergen is present in the cedar pollen in an amount of about 1/50-1/5 of the cedar pollen allergen having a partial amino acid sequence of Asp-Asn-Pro-Ile-Asp-Ser- beginning at its N-terminal as disclosed in the Japanese Patent Laid-Open No. 156,926/89 and (iii) A hyposensitization agent comprising the novel cedar pollen allergen covalently attached to a saccharide attains the object of the present invention.

The cedar pollen allergen as referred to in the present invention includes those prepared from pollens of Japanese cedars (*Cryptomeria japonica*) such as "Omote Sugi (original type of Japanese cedar)" and "Ura Sugi (subspecies of Japanese cedar)", preferably, those having a partial amino acid sequence of Ala-Ile-Asn-Ile-Phe-Asn-, more particularly, Ala-Ile-Asn-Ile-Phe-Asn-Val-Glu-Lys-Tyr- beginning at its N-terminal.

The saccharides freely usable in the present invention include homoglycans, heteroglycans and conjugated polysaccharides, for example, starch, amylose, dextran, polysucrose, pullulan, elsinan, curdlan, gum arabic, gum tragacanth, guar gum, xanthan gum, carrageenan, pectin, cellulose, glucomannan, chitosan and lipopolysaccharide, and their derivatives and partial hydrolysates, having an average molecular weight usually in the range of 500–10,000,000, preferably, in the range of 10,000–1,000,000.

A hyposensitization agent comprising a cedar pollen allergen covalently attached to a water-soluble non-ionic glycan, mainly composed of repeating maltotriose units, such as pullulan, elsinan and their partial hydrolysates prevents an anaphylaxis which may be induced by intact cedar pollen allergen, as well as facilitating the preparation of a more effective hyposensitization agent for cedar pollinosis.

Conjugated polysaccharides derived from microorganisms such as those of the genera *Escherichia*, *Salmonella* and *Serratia*, and partial hydrolyzates of such polysaccharides can be favorably used as a percutaneous or permucosal hyposensitization agent because the conjugate of a cedar pollen allergen and the polysaccharides or their partial hydrolysates easily binds to a tissue such as a mucous membrane.

Any procedure can be employed in the present invention as long as it forms a covalent bonding between a cedar pollen allergen and a saccharide. For example, diazo coupling-, peptide-, alkylation-, cross-linking-, amide coupling-, periodate oxidation- and disulfide-coupling-methods can be employed.

In the diazo coupling method, a cedar pollen allergen is allowed to react with an activated saccharide obtained by introducing an aromatic amino group, for example, p-aminobenzyl-, p-aminobezoyl-, m-aminobenzyl-, m-aminobezoyl-, m-aminoanisole-, m-aminobenzyloxy methyl-, 3-(p-aminophenoxy)-2-hydroxy-propionyl- and 3-(p-amino-m-methyl anilino)-5-chloro-triazinyl-groups into a saccharide in conventional manner.

In the peptide method, a cedar pollen allergen is allowed to react with an activated saccharide, such as sugar carbonate and cyanogen bromide-activated saccharide, which is a derivative of a saccharide bearing a carboxyl group obtained by allowing it to react with azide, acid chloride, carbodiimide or isocyanate.

In the alkylation method, a cedar pollen allergen is allowed to react with an alkyl halide derivative of a saccharide which has been introduced with a group, for example, chloroacetyl-, bromoacetyl-, iodoacetyl- and triazinyl-halide-groups.

In the cross-linking method, a cedar pollen allergen is allowed to react with a saccharide together with a polyfunctional reagent, for example, glutaraldehyde, glyoxal, succinaldehyde, hexamethylene diisocyanate, toluene-2,4-diisocyanate, bis-azobenzidine and N,N'-ethylene-bis-maleimide.

In the amide coupling method, a cedar pollen allergen is allowed to react with an activated saccharide which is obtained by reacting a saccharide having an amino group with a haloacyl halide, for example, bromoacetyl bromide, chlorobutyryl chloride, fluoropropionyl fluoride and iodevaleryl iodide.

The weight ratio of the cedar pollen allergen to the saccharide, both used in the covalent attachment, is usually in the range of 1:0.001–1:1,000, preferably, in the range of 0.01–1:100.

Any reaction condition can be employed as long as the formation of a cedar pollen allergen-saccharide conjugate substantially does not reduce the producibilities of immunoglobulin G and M antibodies which are specific to intact cedar pollen allergen, but extremely reduces the producibility of immunoglobulin E antibody which is responsible for anaphylaxis and allergy: usually, at a temperature of about 0°–100° C. and a pH of about 3–12 for about 0.1–50 hours.

The cedar pollen allergen-saccharide conjugate thus obtained is usually separated and purified by conventional method, for example, filtration, washing, centrifugation, salting-out, dialysis, adsorption and desorption using ion exchange, gel filtration, ion exchange chromatography, affinity chromatography and electrophoresis into a solution or syrup. If necessary, the resultant can be dried into powder. Thus, a hyposensitization agent of cedar pollinosis is obtainable.

The hyposensitization agent can be advantageously used intact or, if necessary, in combination with a stabilizer, antiseptic, adjuvant and filler as an agent for the prevention and treatment of cedar pollinosis.

In comparison with conventional cedar pollen allergen, the hyposensitization agent prepared in this way much more enhances the producibilities of immunoglobulin G and M antibodies which are specific to intact cedar pollen allergen, but extremely reduces the producibility of immunoglobulin E antibody which is specific to the allergen and responsible for anaphylaxis and allergy. Administration of the hyposensitization agent to a cedar pollinosis patient elicits the minimum level of immunoglobulin E antibody which is specific to the allergen.

In comparison with intact cedar pollen allergen, the hyposensitization agent according to the present invention has the following advantages that it is scarcely lost because it does not adsorb on vessels such as glassware: that it is excellently stable: that it is administrable with no anaphylaxis; and that it cuts hyposensitization period to about ⅓ to 1/200.

The hyposensitization agent according to the present invention is usually prepared into an injection, for example, lyophilized injection or liquid injection, and then administered intradermally, subcutaneously, intramuscularly or intraperitoneally to a cedar pollinosis patient at a dose in the range of about 0.01–100,000 ng/shot/adult about 1–2 times/week over a period of about 1–12 months to attain a prescribed hyposensitization.

Furthermore, the hyposensitization agent according to the present invention can be prepared into the form of, for example, percutaneous or permucosal preparations such as troch, collyrium, intranasal nebula, cataplasm, cream or lotion, and the dose and administration frequency can be favorably chosen in order to advantageously attain the object of hyposensitization.

In the local administration method, since the hyposensitization agent according to the present invention also inhibits the binding between a cedar pollen allergen and immunoglobulin E which has been binding to a tissue of a cedar pollinosis patient, the agent exerts an immediate effect on its administered local tissue and instantly relieves the pain of the patient.

Furthermore, the present hyposensitization agent can be advantageously used as an agent for the prevention and treatment of cedar pollinosis, as well as "Hinoki" (Cupressus) pollinosis.

In addition, the present hyposensitization agent can be advantageously used in combination with the hyposensitization agent as disclosed in the Japanese Patent Laid-Open No. 156,926/89 in order to widen the applicability of the present hyposensitization agent to many types of pollinosis patients.

The following experiments will explain the present invention in more detail.

EXPERIMENT I-1

Preparation of cedar pollen allergen

A cedar pollen collected from "Omote Sugi" grown in Chiba, Japan, was added with about 15-folds by weight of 0.125M aqueous sodium hydrogencarbonate solution (pH 8.0). The mixture was subjected to one hour extraction at 4° C. under gentle stirring conditions, followed by centrifugal separation. The residue was further subjected to extraction and centrifugal separation similarly as above. The resultant supernatants were pooled and salted out by the addition of ammonium sulphate to give 80% saturation, and the resultant precipitate was dialyzed and filtered. The filtrate was chromatographed on a column of DEAE-Sephadex ®, commercialized by Pharmacia LKB Biotechnology AB, Uppsala, Sweden. The unadsorbed fraction was collected, chromatographed on a column of CM-Sephadex ®, commercialized by Pharmacia LKB Biotechnology AB, Uppsala, Sweden, and eluted with phosphate buffered saline (pH 7.0). Then, the resultant solution was chromatographed on a column of Mono S ®, commercialized by Pharmacia LKB Biotechnology AB, Uppsala, Sweden, and eluted with Tris-HCl buffer (pH 7.0) to separate a solution containing a purified cedar pollen allergen which exhibits a high affinity to both immunoglobulin E antibody of a cedar pollinosis patent and anti cedar pollen allergen mouse monoclonal antibody in the yield of about 0.001% against the material cedar pollen based on dry solid.

The cedar pollen allergen of the present invention was isolated and eluted from a Mono S ® column. In contrast to the cedar pollen allergen disclosed in the Japanese Patent Laid-Open No. 156,926/89, which was eluted from the column at a concentration of about 0.25M sodium chloride, the cedar pollen allergen according to the present invention was eluted from the column at a concentration of about 0.40M sodium chloride, resulting in a yield of about 1/20 of the allergen as disclosed in the Japanese Patent Laid-Open No. 156,926/89.

The cedar pollen allergen according the present invention exhibited a molecular weight of about 40,000±5,000 on SDS-polyacrylamide gel electrophoresis (SDS-PAGE), and an isoelectric point of about 9.5.

The cedar pollen allergen was degraded by a gas-phase protein sequencer and identified by a high-performance liquid chromatography as described in *The Journal of Biological Chemistry*, Vol. 256, pp. 7990-7997 (1981), followed by determining a partial amino acid sequence of the allergen. As a result, it was found that the cedar pollen allergen had a partial amino acid sequence of alanine-isoleucine-asparagine-isoleucine-phenylalanine-asparagine-valine-glutamic acid-lysine-tyrosine- beginning at its N-terminal. Each amino acid residue in the partial amino acid sequence is an optical isomer in L-configuration, and the partial amino acid sequence may be abbreviated as Ala-Ile-Asn-Ile-Phe-Asn-Val-Glu-Lys-Tyr- in the specification.

EXPERIMENT I-2

Preparation of cedar pollen allergen-pullulan conjugate

One hundred milliliters of 2 w/v % pullulan aqueous solution, average molecular weight of 200,000, was added with 2 ml of 1.7 w/v % cyanuric chloride in acetone. The mixture solution was allowed to stand at 5° C. or lower in ice-chilled water, adjusted to pH 7.0 by the addition of 5% sodium carbonate aqueous solution, and allowed to react for 2 hours while retaining the temperature and pH. Then, the reaction mixture was dialyzed overnight against 4° C. water while retaining the pH. Thus, an activated-pullulan solution was obtained. Thirty milliliters of the activated-pullulan solution was added with 40 ml of a solution containing about 1 mg/ml of a purified cedar pollen allergen obtained by the method in Experiment I-1. The mixture was allowed to stand first at pH 7.0 and 37° C. for 5 hours while stirring, then at 5° C. overnight. The resultant mixture was added with 6 g glycine, allowed to stand for 10 hours while stirring, dialyzed against 0.01M acetate buffer (pH 5.0), and chromatographed on a column of CM-Sephadex ®. The unadsorbed fraction was membrane-filtered to obtain an allergen-pullulan conjugate.

The yield of the product was about 60% against the cedar pollen allergen protein. Unlike intact cedar pollen allergen, the product is easily handleable because it is excellently stable and scarcely lost by its adsorption on glassware and metalware.

EXPERIMENT I-3

Administration test on animal

Experiment I-3-1

Test on prophylactic activity

One fifth ml of physiological saline containing as the allergen 1 µg of an allergen-pullulan conjugate obtained by the method in Experiment I-2 was intraperitoneally administered to a group of six BALB/c female mice (10 to 12 week-old) once a week over a period of 3 weeks. One-week after the intraperitoneal administration, 0.2 ml of physiological saline containing 1 µg of a cedar pollen allergen, obtained by the method in Experiment I-1, and 4 mg aluminum hydroxide as the adjuvant was administered to each mouse in the same manner as described in the above.

The amounts of immunoglobulin G, M and E antibodies, specific to intact cedar pollen allergen, were determined with a blood sample which had been collected from mice immediately before the intraperitoneal administration of the mixture of cedar pollen allergen and aluminum hydroxide, and with another blood sample which had been collected from the mice one-week after the intraperitoneal administration of the mixture.

As control, in place of the allergen-pullulan conjugate, a mixture containing 1 µg of a cedar pollen allergen prepared by the method in Experiment I-1 and 40 µg of a fresh preparation of the same pullulan as used in Experiment I-2 was administered to each mouse.

The levels of immunoglobulin G and M antibodies were evaluated by the antibody titers determined by the enzyme immunoassay (EIA) described in *The Journal of Biochemistry*, Vol. 92, pp. 1413-1424 (1982), and the level of immunoglobulin E antibody was evaluated by the antibody titer determined by the passive cutaneous anaphylaxis (PCA) reaction described in *Life Science*, Vol. 8, Part II, pp. 813-820 (1969). The results were as shown in Table 1.

TABLE 1

| | Period for collecting blood | | | | |
|---|---|---|---|---|---|
| | Immediately before administration of mixture of cedar pollen allergen and aluminum hydroxide | | One-week after administration of mixture of cedar pollen allergen and aluminum hydroxide | | |
| | Immunoglobulin | | | | |
| Hyposensitization agent | G & M | E | G & M | E | Note |
| Cedar pollen allergen-pullulan conjugate | 230 | 0 | 960 | 3 | Present invention |
| Mixture of cedar pollen | 26 | 22 | 270 | 330 | Control |

TABLE 1-continued

| | Period for collecting blood | | | | |
|---|---|---|---|---|---|
| | Immediately before administration of mixture of cedar pollen allergen and aluminum hydroxide | | One-week after administration of mixture of cedar pollen allergen and aluminum hydroxide | | |
| | Immunoglobulin | | | | |
| Hyposensitization agent | G & M | E | G & M | E | Note |
| allergen and pullulan | | | | | |

Annotation:
Each value is an average of immunoglobulin antibody titers of immunoglobulin antibodies produced in a group of 6 mice.

As evident from the results in Table 1, unlike the mixture of intact cedar pollen allergen and pullulan, the cedar pollen allergen-pullulan conjugate according to the present invention can be favorably used as a hyposensitization agent for the prevention of cedar pollinosis.

EXPERIMENT I-3-2

Test on therapeutic activity

One fifth ml of physiological saline containing 1 μg of a cedar pollen allergen obtained by the method in Experiment I-1 and 4 mg aluminum hydroxide as the adjuvant was intraperitoneally administered to a group of six BALB/c female mice (10 to 12 week-old) once a week over a period of 3 weeks. Two-weeks after the intraperitoneal administration, 0.2 ml of physiological saline containing as the allergen 1 μg of an allergen-pullulan conjugate obtained by the method in Experiment I-2 was administered in the same manner as described in the above to each mouse 3-times a week over a period of 3 weeks.

Furthermore, the formation of immunoglobulin E antibody was boosted by administering a mixture of cedar pollen allergen and aluminum hydroxide to the mice.

The levels of immunoglobulin G, M and E antibodies were determined with a blood sample collected from mice immediately before and one-week after the final intraperitoneal administration of the cedar pollen allergen-pullulan conjugate, and another blood sample which had been collected from mice one-week after the induction of immunoglobulin E antibody by the intraperitoneal administration of the mixture of cedar pollen allergen and aluminum hydroxide.

As control, a mixture of cedar pollen allergen and pullulan was used similarly as in Experiment I-3-1 in place of the cedar pollen allergen-pullulan conjugate. The results were as shown in Table 2.

the present invention can be favorably used as a hyposensitization agent for the treatment of cedar pollinosis.

Furthermore, a physiological saline containing the above cedar pollen allergen-aluminum hydroxide conjugate was administered orally, intranasally, intradermally or subcutaneously to guinea pigs, rats or mice which had been presensitized by the administration of a mixture of intact cedar pollen allergen and aluminum hydroxide to form immunoglobulin E antibody. One-hour after the administration, intact cedar pollen allergen was administered to mouths, nasal cavities, intradermal tissues or subcutaneous tissues of the animals to observe no allergic reaction which should be developed in the animals.

As described hereinbefore, a cedar pollen allergen-saccharide conjugate according to the present invention can be favorably used as a hyposensitization agent for the prevention and treatment of cedar pollinosis because the conjugate exerts a high hyposensitivity with no anaphylaxis.

EXPERIMENT II-1

Preparation of cedar pollen allergen-lipopolysaccharide conjugate

One ml of 10 mM calcium phosphate solution containing 10 mg of lipopolysaccharide derived from a microorganism of the species *Escherichia coli* was added with 60 μl of 100 mM sodium periodate, and the mixture was allowed to react at ambient temperature for 20 minutes to cleavage a saccharide chain of the lipopolysaccharide. The resultant was dialyzed overnight against 1M glycine-HCl buffer (pH 4.4) kept at 4° C., and the resultant excessive amount of sodium periodate was removed, followed by adjusting the pH to about 9.5 by the addition of 0.1M sodium hydrogencarbonate buffer.

Furthermore, 10 mg of a cedar pollen allergen obtained by the method in Experiment I-1 was dissolved in

TABLE 2

| | Period for collecting blood | | | | | | |
|---|---|---|---|---|---|---|---|
| | Immediately before administration of cedar pollen allergen-pullulan conjugate | | One-week after administration of cedar pollen allergen-pullulan conjugate | | One-week after production of immunoglobulin E antibody by booster shot | | |
| | Immunoglobulin | | | | | | |
| Hyposensitization agent | G & M | E | G & M | E | G & M | E | Note |
| Cedar pollen allergen-pullulan conjugate | 360 | 170 | 2,500 | 40 | 5,960 | 40 | Present invention |
| Mixture of cedar pollen allergen and pullulan | 370 | 170 | 470 | 340 | 2,780 | 1,300 | Control |

Annotation:
Each value is an average of immunoglobulin antibody titers of immunoglobulin antibodies produced in a group of 6 mice.

As evident from the results in Table 2, unlike a mixture of intact cedar pollen allergen and pullulan, the cedar pollen allergen-pullulan conjugate according to 1 ml of phosphate buffer (pH 9.5), and the mixture was mixed with the lipopolysaccharide solution prepared in the above to form a Schiff base.

Thereafter, the resultant was added with sodium boron hydride to complete the conjugate-formation reaction, and the reaction mixture was chromatographed on a column of Sephadex ® G-100 to recover fractions containing a cedar pollen allergen-lipopolysaccharide conjugate. The fractions were pooled and membrane-filtered to obtain a cedar pollen allergen-lipopolysaccharide conjugate.

The yield of the product was about 40% against the cedar pollen allergen protein.

Unlike intact cedar pollen allergen, the product is easily handleable because it is excellently stable and scarcely lost by its adsorption on glassware.

EXPERIMENT II-2

Administration test on animals

One ml of physiological saline containing as the allergen 10 µg of an allergen-lipopolysaccharide conjugate obtained by the method in Experiment II-1 was orally administered to a group of six BALB/c female mice (10 to 12 week-old) 3-times a week over a period of 3 weeks. One-week after the administration, blood were sampled from the mice, and the amounts of immunoglobulin A, G and E antibodies in the blood samples were determined.

As control, in place of the cedar pollen allergen-lipopolysaccharide conjugate, a mixture of intact cedar pollen allergen and lipopolysaccharide was administered to each mouse. The levels of immunoglobulin A and G antibodies were evaluated by the antibody titers determined by the EIA method described in *Journal of Immunological Methods*, Vol. 6, pp. 355-362 (1975), and the level of immunoglobulin E antibody was evaluated by the antibody titers determined by the PCA reaction used in Experiment I-3-1. The results were as shown in table 3.

TABLE 3

| Hyposensitization | Immunoglobulin | | | Note |
|---|---|---|---|---|
| agent | A | G | E | |
| Cedar pollen allergen-lipopolysaccharide conjugate | 260 | 62 | 0 | Present invention |
| Mixture of cedar pollen allergen and lipopolysaccharide | 5 | 17 | 17 | Control |

Annotation:
Each value is an average of immunoglobulin antibody titers of immunoglobulin antibodies produced in a group of 6 mice.

As evident from the results in Table 3, unlike a mixture of intact cedar pollen allergen and lipopolysaccharide, the present cedar pollen allergen-lipopolysaccharide conjugate is favorably used as the hyposensitization agent for the prevention and treatment of cedar pollinosis.

Furthermore, the hyposensitization agent has the following feature: A physiological saline containing the above cedar pollen allergen-lipopolysaccharide conjugate was sprayed into mouths and nasal cavities of mice which had been presensitized by the administration of a mixture of intact cedar pollen allergen and aluminum hydroxide to form immunoglobulin E antibody. Thirty-minutes after the spraying, the mice were further sprayed with a cedar pollen allergen to observe no allergic reaction which should be developed in the mice.

In general, since a cedar pollen allergen-conjugated polysaccharide conjugate such as a cedar pollen allergen-lipopolysaccharide conjugate has a higher binding ability to a mucous membrane and stays longer on a local tissue than a cedar pollen allergen-homoglycan conjugate such as a cedar pollen allergen-pullulan conjugate, the cedar pollen allergen-conjugated polysaccharide conjugate is highly absorptive into a mucous membrane, and exerts a superior hyposensitization effect as a hyposensitization agent in the form of oral, percutaneous or permucosal agent.

Examples of the present invention will be described hereinafter.

EXAMPLE 1

Example 1(1)

Preparation of cedar pollen allergen

A cedar pollen collected from "Ura Sugi" grown in Akita, Japan, was prepared into a purified cedar pollen allergen in solution by the method in Experiment I-1 in the yield of about 0.001% against the weight of the material cedar pollen based on dry solid. The purified cedar pollen allergen had a molecular weight of about $40,000 \pm 5,000$ on SDS-polyacrylamide gel electrophoresis, and an isoelectric point of about 9.5.

After detection of a partial amino acid sequence of the cedar pollen allergen in accordance with the method in Experiment I-1, the partial amino acid sequence consisting of 10-amino acid residues beginning at its N-terminal was identical with that of the allergen prepared from "Omote Sugi" described in Experiment I-1.

Example 1(2)

Hyposensitization agent

Five grams of pullulan having an average molecular weight of about 140,000 was dissolved in 400 ml of water, and the resultant solution was adjusted to pH 10.7 by the addition of 1N sodium hydroxide. The solution was then allowed to react with 3 g cyanogen bromide for 1 hour while gradually adding it to the solution and retaining the pH. The reaction mixture was adjusted to pH 5.0 by the addition of 1N hydrochloric acid, and dialyzed against cold water while retaining the pH. Thus, an activated-pullulan solution was obtained.

To the activated-pullulan solution was added 200 ml of a cedar pollen allergen solution prepared by the method in Example 1(1), and the mixture was allowed to react at ambient temperature for 24 hours. After completion of the reaction, the reaction mixture was poured with acetone (1:3 by volume), and the resultant precipitate was collected, dissolved in 0.01M acetate buffer (pH 5.0), and centrifugally separated to remove the insoluble residue. The remaining supernatant was chromatographed on a column of CM-Sephadex ®, and the unadsorbed fraction was membrane-filtered. The filtrate was bottled into ampules to obtain a liquid hyposensitization agent containing a cedar pollen allergen-pullulan conjugate.

The yield was about 70% against the cedar pollen allergen protein. The product can be favorably used in the prevention and treatment of cedar pollinosis because of its high hyposensitivity with no anaphylaxis.

Unlike intact cedar pollen allergen, the product is easily handleable because it is excellently stable and scarcely lost by its adsorption on glassware and metalware.

EXAMPLE 2

Fifty-two grams of a pullulan partial hydrolysate having an average molecular weight of about 10,000 was dissolved in 110 ml of dimethylformamide while heating. The mixture was cooled to ambient temperature, and poured with 10 ml of pyridine, and added with 1.0 g of 4-nitrobenzoyl chloride while stirring, followed by standing at ambient temperature for 17 hours. The resultant mixture was added with 2-volumes of n-propyl alcohol to obtain a precipitate which was then collected and dissolved in dimethylformamide. The above precipitation was repeated 3-times, and the resultant precipitates were pooled and dissolved in 100 ml of 5 w/v % sodium hydrosulfite aqueous solution. The mixture was allowed to stand at 80° C. for 30 minutes, decolored with activated charcoal and precipitated by the addition of 2-volumes of n-propyl alcohol. The resultant precipitate was dissolved in water, dialyzed overnight against water, cooled to 2° C. or lower, and added with hydrochloric acid to give a final concentration of about 0.1N while stirring. Then, the resultant mixture was added with sodium nitrite to give a concentration of about 1 w/v %, allowed to react for 30 minutes, and dialyzed against distilled water at 2° C. or lower for 2 hours to obtain an activated pullulan partial hydrolysate.

To the activated pullulan partial hydrolysate was added 20 ml of a solution containing a cedar pollen allergen from "Omote Sugi" obtained by the method in Experiment I-1, and the mixture was adjusted to pH 8.5 by the addition of a sodium carbonate aqueous solution. Then, the mixture was allowed to effect the coupling reaction at 4° C. for 2 hours while stirring, purified similarly as in Example 1, and bottled into ampules to obtain a liquid hyposensitization agent containing a cedar pollen allergen-pullulan partial hydrolysate conjugate.

The yield of the product was about 60% against the cedar pollen allergen protein.

Similarly as the product in Example 1, the liquid hyposensitization agent is favorably used in the prevention and treatment of cedar pollinosis and is easily handleable because it is excellently stable and scarcely lost by its adsorption on glassware and metalware.

EXAMPLE 3

Ten grams of elsinan, average molecular weight of about 200,000, was dissolved in 200 ml of distilled water while heating. The resultant was cooled to ambient temperature and added with 5 g hexamethylenediamine. The mixture solution was adjusted to pH 11.0 by the addition of 1N sodium hydroxide solution, allowed to stand at 20° C. or lower in ice-chilled water, and added with 5 g cyanogen bromide while retaining the temperature and pH. The resultant mixture was allowed to react for 30 minutes while stirring and retaining the temperature and pH. The reaction mixture was dialyzed against 4° C. distilled water for one hour to obtain an activated-elsinan solution.

The activated-elsinan solution was poured with 2 ml of 25 w/v % glutaraldehyde and 60 ml of a solution containing a cedar pollen allergen from "Omote Sugi" obtained by the method in Experiment I-1, and the mixture was added with 10 ml of 1M acetate buffer (pH 5.0) to effect the coupling reaction at 4° C. for 24 hours while stirring. To the reaction mixture was added glycine to give a concentration of 1M, and the resultant was allowed to stand at ambient temperature for 24 hours, followed by centrifugal separation. The supernatant was subjected to gel filtration, and fractions containing a cedar pollen allergen-elsinan conjugate were pooled, concentrated and membrane-filtered. The filtrate was bottled, lyophilized and sealed to obtain a solid hyposensitization agent containing the cedar pollen allergen-elsinan conjugate.

The yield of the product was about 50% against the cedar pollen allergen protein.

Similarly as the product in Example 1, the product is easily handleable and usable in the prevention and treatment of cedar pollinosis.

EXAMPLE 4

Two hundred milliliters of 1 w/v % carboxymethyl cellulose aqueous solution, average molecular weight of about 20,000, was added with 2 g of 1-ethyl-3-(3-dimethylamino-propyl)-carbodiimide-methiodide, and the mixture solution was adjusted to pH 4.0 by the addition of 1N hydrochloric acid and allowed to react at ambient temperature for 2 hours while stirring and retaining the pH. The reaction mixture was dialyzed overnight against distilled water to obtain an activated-carboxymethyl-cellulose solution.

The activated-carboxymethyl-cellulose solution was added with 50 ml of a solution containing a cedar pollen allergen from "Ura Sugi" obtained by the method in Example 1(1), and the activated carboxymethyl cellulose and the cedar pollen allergen were allowed to effect the coupling reaction at ambient temperature overnight while stirring and retaining the pH at 4.5. Then, the resultant conjugate was purified similarly as in Example 3, and bottled into ampules to obtain a liquid hyposensitization agent containing the cedar pollen allergen-carboxymethyl cellulose conjugate.

The yield of the product was about 30% against the cedar pollen allergen protein.

Although the product is slightly lower in producibilities of immunoglobulin G and M antibodies, which are specific to intact cedar pollen allergen, than a cedar pollen allergen-pullulan conjugate and a cedar pollen allergen-elsinan conjugate, the handleability of the product is satisfiable because it does not produce immunoglobulin E antibody which is specific to the allergen, and because it is usable as a hyposensitization agent for the prevention and treatment of cedar pollinosis.

EXAMPLE 5

One hundred mg of a lipopolysaccharide derived from a microorganism of the genus Salmonera was added with 25 ml of 50% saturation of sodium acetate kept at about 4° C., and the mixture was adjusted to pH 9.0 by the addition of 0.5N sodium hydroxide, and gradually added with a mixture (pH about 8.5) containing 20 μl of bromoacetyl bromide and 1 ml of anhydrous dioxane. The resultant mixture was then adjusted to pH about 4.5 by the addition of 6N hydrochloric acid, and dialyzed against 4° C. water for 5 days to prepare an activated-lipopolysaccharide solution.

To the activated-lipopolysaccharide solution was added 40 ml of a solution containing a cedar pollen allergen derived from "Ura Sugi" grown in Akita prepared by the method in Example 1(1), and the mixture was allowed to react at 25° C. for 2 days while stirring and keeping the pH at 4.5. After completion of the reaction, the reaction mixture was purified similarly as in Example 3, and bottled into ampules to obtain a liquid hyposensitization agent containing a cedar pollen allergen-lipopolysaccharide conjugate.

The yield of the product was about 35% against the cedar pollen allergen protein.

The product is easily handleable and favorably used as an agent for the prevention and treatment of cedar pollinosis.

Furthermore, since the product using a lipopoly-saccharide as the saccharide, advantageously binds to a mucous membrane and stays on a local tissue for a relatively long period of time, the product is highly absorptive into a mucous membrane, and exerts a strong hyposensitization effect as a percutaneous or permucosal hyposensitization agent in the form of an oral or intranasal agent.

Effect of the invention

As evident from the above, the novel cedar pollen allergen according to the present invention, more particularly, the hyposensitization agent comprising a saccharide covalently attached to a cedar pollen allergen having a partial amino acid sequence of Ala-Ile-Asn-Ile-Phe-Asn- beginning at its N-terminal is administrable to a cedar pollinosis patient with no anaphylaxis, and cuts hyposensitization period to about ⅓ to 1/200. The above reason is that the hyposensitization agent, when compared with an intact cedar pollen allergen, extremely accelerates the production of immunoglobulin G and M antibodies which are specific to intact cedar pollen allergen, but extremely reduces the production of immunoglobulin E antibody which is specific to the allergen.

Furthermore, the present hyposensitization agent can be advantageously used as a local administration agent such as a percutaneous or permucosal agent because the present hyposensitization agent instantly relieves the pain of the patient, and inhibits the antigen and antibody reaction occurring between a cedar pollen allergen and immunoglobulin E which has been binding to a tissue of a cedar pollinosis patient.

In addition, the present hyposensitization agent has a great significance in the field because it is scarcely lost by its adsorption on vessels such as glassware and metalware, and because its stability and handleability are both satisfiable as compared with intact cedar pollen allergen.

While there has been described what is at present considered to be the preferred embodiments of the invention, it will be understood that various modifications may be made therein, and it is intended to cover in the appended claims all such modifications as fall within the true spirit and scope of the invention.

We claim:

1. A conjugate, which comprises a saccharide covalently attached to a cedar pollen allergen having a partial amino acid sequence of Ala-Ile-Asn-Ile-Phe-Asn- beginning at its N-terminus.

2. The conjugate as claimed in claim 1, wherein said cedar pollen allergen has a partial amino acid sequence of Ala-Ile-Asn-Ile-Phe-Asn-Val-Glu-Lys-Tyr- beginning at its N-terminus.

3. The conjugate as claimed in claim 1, wherein said cedar pollen allergen has been prepared from a pollen of Japanese cedar (*Cryptomeria japonica*).

4. The conjugate as claimed in claim 1, wherein said molecular weight of said cedar pollen allergen is about 40,000±5,000 on SDS-polyacrylamide gel electrophoresis.

5. The conjugate as claimed in claim 1, wherein the isoelectric point of said cedar pollen allergen is about 9.5.

6. The conjugate as claimed in claim 1, wherein the weight ratio of said cedar pollen allergen to said saccharide is in the range of 1:0.001–1:1,000.

7. The conjugate as claimed in claim 1, wherein said saccharide is a glycan mainly composed of repeating maltotriose units.

8. The conjugate as claimed in claim 7, wherein said glycan is pullulan, elsinan or their partial hydrolysate.

9. The conjugate as claimed in claim 1, wherein the molecular weight of said saccharide is in the range of 500–10,000,000.

10. The conjugate as claimed in claim 1, wherein said saccharide is a lipopolysaccharide or its partial hydrolysate.

11. The conjugate as claimed in claim 10, wherein said lipopolysaccharide is derived from a microorganism of the genus Escherichia, Salmonella or Serratia.

12. A hyposensitization agent, which comprises a saccharide covalently attached to a cedar pollen allergen having a partial amino acid sequence of Ala-Ile-Asn-Ile-Phe-Asn- beginning at its N-terminus as an effective component, and a pharmaceutically acceptable carrier.

13. The agent as claimed in claim 12, wherein said cedar pollen allergen has a partial amino acid sequence of Ala-Ile-Asn-Ile-Phe-Asn-Val-Glu-Lys-Tyr- beginning at its N-terminus.

14. The agent as claimed in claim 12, wherein said cedar pollen allergen has been prepared from a pollen of Japanese cedar (*Cryptomeria japonica*).

15. The agent as claimed in claim 12, wherein the molecular weight of said cedar pollen allergen is about 40,000±5,000 on SDS-polyacrylamide gel electrophoresis.

16. The agent as claimed in claim 12, wherein the isoelectric point of said cedar pollen allergen is about 9.5.

17. The agent as claimed in claim 12, wherein the weight ratio of said cedar pollen allergen to said saccharide is in the range of 1:0.001–1:1,000.

18. The agent as claimed in claim 12, wherein said saccharide is a glycan mainly composed of repeating maltotriose units.

19. The agent as claimed in claim 18, wherein said glycan is pullulan, elsinan or their partial hydrolysate.

20. The agent as claimed in claim 12, wherein the molecular weight of said saccharide is in the range of 500–10,000,000.

21. The agent as claimed in claim 12, wherein said saccharide is a lipopolysaccharide or its partial hydrolysate.

22. The agent as claimed in claim 21, wherein said lipopolysaccharide is derived from a microorganism of the genus Escherichia, Salmonella or Serratia.

23. The agent as claimed in claim 12, wherein said agent is for the treatment of cedar pollinosis.

24. The agent as claimed in claim 12, wherein said agent is for the prevention of cedar pollinosis.

25. The agent as claimed in claim 12, wherein said agent is in the form of troch, collyrium, intranasal nebula, cataplasm, cream or lotion.

26. The agent as claim in claim 12, wherein said agent is used at a dose of 0.01–100,000 ng/shot/adult.

27. The agent as claimed in claim 12, wherein said pharmaceutically acceptable carrier is a member selected from the group consisting of stabilizer, antiseptic, adjuvant and filler.

* * * * *